(12) United States Patent
Rousseau (10) Patent No.: US 9,989,546 B2
(45) Date of Patent: Jun. 5, 2018

(54) ANALYSIS DEVICE FOR IN VITRO DIAGNOSTICS

(71) Applicant: ALAIN ROUSSEAU-TECHNIQUES & INNOVATIONS (ARTEION), Paris (FR)

(72) Inventor: Alain Rousseau, Paris (FR)

(73) Assignee: ARTEION, Paris (FR)

( * ) Notice: Subject to any disclaimer, the term of this patent is extended or adjusted under 35 U.S.C. 154(b) by 0 days. days.

(21) Appl. No.: 14/442,067

(22) PCT Filed: Oct. 30, 2013

(86) PCT No.: PCT/FR2013/052597
§ 371 (c)(1),
(2) Date: May 11, 2015

(87) PCT Pub. No.: WO2014/072616
PCT Pub. Date: May 15, 2014

(65) Prior Publication Data
US 2015/0285829 A1    Oct. 8, 2015

(30) Foreign Application Priority Data

Nov. 9, 2012 (FR) .................................... 12 60661

(51) Int. Cl.
G01N 35/02    (2006.01)
G01N 35/04    (2006.01)
(Continued)

(52) U.S. Cl.
CPC ........... *G01N 35/04* (2013.01); *G01N 35/026* (2013.01); *G01N 2035/00524* (2013.01);
(Continued)

(58) Field of Classification Search
CPC . G01N 2035/00524; G01N 2035/0415; G01N 2035/0465
See application file for complete search history.

(56) References Cited

U.S. PATENT DOCUMENTS 4,609,017 A * 9/1986 Coulter .............. G01N 35/0095
141/1
5,207,986 A * 5/1993 Kadota ................... G01N 35/02
198/468.11
(Continued)

FOREIGN PATENT DOCUMENTS

CN    101376087 A    3/2009
CN    101893640 A    11/2010
(Continued)

OTHER PUBLICATIONS

International Search Report dated Feb. 27, 2014 re: Application No. PCT/FR2013/052597.

*Primary Examiner* — P. Kathryn Wright
(74) *Attorney, Agent, or Firm* — Cantor Colburn LLP (57) ABSTRACT

This analysis device includes at least one rack intended to receive a plurality of containers containing samples of biological liquid to be analyzed, a loading module arranged to move the at least one rack between a loading position and a first intermediate position, a shaking module arranged to move the at least one rack between the first intermediate position and a second intermediate position and to shake the at least one rack, an unloading module arranged to move the at least one rack between the second intermediate position and an unloading position, where the loading and unloading modules are arranged to move the at least one rack respectively along a first and a second movement directions transverse to the plane of the at least one rack, and where the shaking module is arranged such that the at least one rack
(Continued)

extends substantially along a same orientation in the first and second intermediate positions.

15 Claims, 9 Drawing Sheets (51) Int. Cl.
*G01N 35/10* (2006.01)
*G01N 35/00* (2006.01)
(52) U.S. Cl.
CPC ................ *G01N 2035/0403* (2013.01); *G01N 2035/0415* (2013.01); *G01N 2035/0444* (2013.01); *G01N 2035/0465* (2013.01)

(56) References Cited

U.S. PATENT DOCUMENTS

| | | | | |
|---|---|---|---|---|
| 5,856,194 A | * | 1/1999 | Arnquist | ............ G01N 35/0092 422/63 |
| 2002/0021983 A1 | * | 2/2002 | Comte | ................ B01F 11/0017 422/65 |
| 2005/0196320 A1 | | 9/2005 | Veiner et al. | |
| 2011/0124128 A1 | | 5/2011 | Oosterbroek et al. | |

FOREIGN PATENT DOCUMENTS

| | | |
|---|---|---|
| EP | 1174717 A1 | 1/2002 |
| FR | 2907905 A1 | 5/2008 |
| WO | 2008059685 A1 | 5/2008 |
| WO | WO 2013143406 A1 * 10/2013 | ............. G01N 35/04 |

\* cited by examiner

ANALYSIS DEVICE FOR IN VITRO DIAGNOSTICS

TECHNICAL FIELD

The present invention relates to an analysis device for in vitro diagnosis, and more particularly a whole-blood analysis device.

BACKGROUND

The document FR 2 907 905 discloses an analysis device for in vitro diagnosis comprising:
- a plurality of racks intended to receive containers equipped with sealing elements and containing samples of biological liquid to be analyzed,
- a loading module arranged to move each rack between a loading position and a first intermediate position,
- a shaking module arranged to move each rack between the first intermediate position and a second intermediate position and to shake said rack,
- an unloading module arranged to move each rack between the second intermediate position and an unloading position, and
- a sampling module arranged to take samples of biological liquid in the containers received in the at least one rack.

According to the document FR 2 907 905, the loading module comprises a storage element provided to enable a stacking of racks substantially horizontally oriented, and extracting means arranged to extract the racks out of the storage element in the direction of the shaking module. The extracting means are more particularly arranged to move each rack in translation along a horizontal direction and parallel to the plane of said rack.

Such a flat positioning of the racks in the storage element requires a manual loading of the racks in the latter, which involves on the one hand tedious manipulations for an operator, and on the other a low analysis rate.

In addition, according to the document FR 2 907 905, the shaking module comprises moving and tilting means arranged to move a rack from an introduction position in the shaking module wherein said rack extends substantially horizontally to a removal position of said shaking module wherein said rack extends substantially vertically.

By this configuration of the loading, unloading and shaking modules, the analysis device described in the document FR 2 907 905 has a complex structure and high manufacturing costs.

BRIEF SUMMARY

The present invention aims to overcome these drawbacks.

The technical problem at the basis of the invention concerns providing an analysis device for in vitro diagnosis which is of simple and economical structure, while ensuring a high analysis rate.

To this end, the present invention relates to an analysis device for in vitro diagnosis, comprising:
- at least one rack intended to receive a plurality of containers equipped with sealing elements and containing samples of biological liquid to be analyzed,
- a loading module arranged to move the at least one rack between a loading position and a first intermediate position along a first direction transverse to the plane of the at least one rack,
- a shaking module arranged to move the at least one rack between the first intermediate position and a second intermediate position and to shake the at least one rack, the shaking module being arranged so that the at least one rack extends substantially along a same orientation in the first and second intermediate positions
- an unloading module arranged to move the at least one rack between the second intermediate position and an unloading position along a second movement direction transverse to the plane of the at least one rack, and
- a sampling module arranged to take samples of biological liquid in the containers received in the at least one rack, the shaking module including:
- guiding means arranged to guide in translation the at least one rack between the first and second intermediate positions along a guiding direction,
- translational driving means arranged to drive in translation the at least one rack between the first and second intermediate positions along said guiding direction, and
- pivoting means arranged to pivotally drive the guiding means around a pivot axis.

Such a configuration of the shaking module and of the loading and unloading modules enables to ensure a movement of the racks between the loading and the unloading positions using simple moving means, which improves the reliability and reduces the manufacturing costs of the analysis device according to the invention.

Further, such a configuration of the loading and unloading modules enables to ensure automatic loading and unloading of the racks into and out of the analysis device according to the invention, for example by disposing loading and unloading conveyors facing respectively the loading and unloading modules. These dispositions enable to ensure high analysis rates.

It should be noted that the analysis device according to the invention may be used to carry out in particular hematology analyses, Complete Blood Count (CBC) analyses, cytology analyses, flow cytometry analyses, immuno-hematology analyses, hemostatic coagulation analyses, or even to prepare blades for automatic observation by microscopic of cells and to determine the sedimentation speed, etc.

According to one embodiment of the invention, the shaking module is arranged such that the at least one rack extends substantially in a same plane in the first and second intermediate positions.

According to one embodiment of the invention, the shaking module is arranged such that the at least one rack extends substantially vertically in the first and second intermediate positions.

In an advantageous manner, the first and second intermediate positions correspond respectively to insertion and removal positions of a rack into and out of the shaking module.

Advantageously, the first and second intermediate positions are respectively disposed at one of the ends of the loading and unloading modules.

According to one embodiment of the invention, the loading and unloading modules are arranged such that the first and second movement directions are substantially perpendicular to the plane of the at least one rack.

According to one feature of the invention, the loading and unloading modules are arranged to maintain the at least one substantially vertical rack, and more particularly the containers received in said rack, during its movements along the first and second movement directions.

According to one embodiment of the invention, the shaking module is arranged to maintain the at least one substantially vertical rack, and more particularly the containers received in said rack, during its movements between the first and second intermediate positions.

According to one embodiment of the invention, the first and second movement directions are substantially parallel.

The loading and unloading modules include for example respectively a first and a second conveyors. The first and second conveyors are advantageously belt or band conveyors.

According to one embodiment of the invention, the guiding direction is substantially perpendicular to the first and second movement directions.

According to one embodiment of the invention, the guiding direction and the first and second movement directions are substantially horizontal when in use.

According to one embodiment of the invention, the guiding means are disposed at the ends of the loading and unloading modules.

According to one embodiment of the invention, the guiding means are arranged to guide laterally in translation the at least one rack between the first and second intermediate positions along the guiding direction.

According to one embodiment of the invention, the shaking module and the loading and unloading modules define a generally U-shaped rack transport path. Advantageously, the rack transport path is substantially horizontal when in use.

Advantageously, the pivot axis of the guiding means is substantially parallel to the guiding direction. In an advantageous manner, the pivot axis of the guiding means is substantially horizontal when in use.

According to one embodiment of the invention, the guiding means include a rack support delimiting a housing in which the at least one rack is able to slide along the guiding direction, the rack support being pivotally mounted around the pivot axis. In an advantageous manner, the housing delimited by the rack support is arranged to simultaneously house a plurality of racks.

According to one embodiment of the invention, the support rack includes a rack introduction portion and a rack removal portion, the translational driving means being arranged to drive in translation the at least one rack received in the housing of the rack support between the rack introduction portion and the rack removal portion.

Advantageously, the rack support extends substantially perpendicularly to the loading and unloading modules.

According to one embodiment of the invention, the rack support is pivotally mounted around the pivot axis between at least a first angular position wherein a rack is able to be inserted into or removed out of the rack support and a second angular position angularly offset from the first angular position, the pivot axis of the rack support being disposed below the housing of the rack support when the rack support is in its first angular position. These dispositions enable to ensure a simple and efficient shaking of the containers contained in a rack disposed in the shaking module.

Advantageously, the rack support extends substantially vertically in its first angular position.

According to one embodiment of the invention, the rack support includes a guiding surface arranged to cooperate with the base of a rack during the sliding of said rack in the housing of the rack support, the pivot axis of the rack support being disposed below the guiding surface when the rack support is in its first angular position.

According to one embodiment of the invention, the rack support includes at least a first guiding wall arranged to cooperate with a lateral wall of a rack during the sliding of said rack in the housing of the rack support, and a retaining wall arranged to cooperate with sealing elements of containers received in said rack so as to retain the containers in said rack during the pivoting of the rack support. Such a configuration of the rack support ensures an optimal guiding of the racks between the first and second intermediate positions, while enabling the use of simple and inexpensive racks.

According to one embodiment of the invention, the rack support further includes a second guiding wall arranged to cooperate with a lower surface of a rack during the sliding of said rack in the housing of the rack support.

According to one embodiment of the invention, the retaining wall is also arranged to cooperate with the sealing elements of the containers received in said rack during the sliding of said rack in the housing of the rack support.

According to one embodiment of the invention, the retaining wall includes a passage orifice intended for the passage of a sampling needle.

According to one embodiment of the invention, the pivoting means are arranged to pivotally drive the guiding means around the pivot axis along an angular displacement comprised between 0 and 160°, and for example between 0 and about 120°.

Advantageously, the rack support is inclined by an angle of about 120° relative to the vertical when it is in its second angular position.

According to one embodiment of the invention, the sampling module is disposed near the shaking module.

According to one embodiment of the invention, the translational driving means are arranged to immobilize the at least one rack in at least one sampling position disposed between the first and second intermediate positions, the sampling module being arranged to take a sample of biological liquid in at least one container received in said rack when said rack is immobilized in the at least one sampling position.

Preferably, the translational driving means are arranged to immobilize the at least one rack in a plurality of sampling positions disposed between the first and second intermediate positions, each sampling position corresponding to a position of said rack wherein the sampling module is arranged to take a sample of biological liquid in one of the containers received in said rack. For example, when N containers are received in the rack, the translational driving means are arranged to immobilize said rack in N distinct sampling positions.

According to one embodiment of the invention, the translational driving means include at least one fork intended to cooperate with a rack received in the housing of the rack support, a guiding rail extending parallel to the guiding direction and on which the fork is slidably mounted, an endless belt, such as an endless toothed belt, connected to the fork, and a driving motor arranged to drive the endless belt.

According to one embodiment of the invention, the shaking module is arranged to immobilize the guiding means in a transfer position wherein the at least one rack is able to be guided in translation between the first and second intermediate positions.

According to one embodiment of the invention, the pivoting means include a driving motor, such as a stepper motor, coupled, for example by means of an endless belt, such as an endless toothed belt, to a pulley secured in rotation to the rack support and of axis coincident with the pivot axis of the rack support.

According to one embodiment of the invention, the analysis device includes detecting means arranged to detect the insertion of a rack in the housing of the rack support, and control means connected to the detecting means and arranged to initiate the pivoting of the rack support when the detecting means have detected the insertion of a rack in the housing of the rack support.

According to one embodiment of the invention, the pivoting means are arranged to pivotally drive the guiding means along a swing movement around the pivot axis. The pivoting means are for example arranged to generate at least twelve swings by minute of the guiding means around the pivot axis, preferably with breaks between the swings such that the air bubble present in each container received in the rack can travel all the height of the container, and thus cause an optimal mixture of the sample.

According to one embodiment of the invention, the pivoting means are arranged to enable a tilting of the rack between a position wherein the rack is oriented upwards and a position wherein the rack is oriented downwards, and more particularly between a position wherein the containers received in the rack are oriented upwards and a position wherein the containers received in the rack are oriented downwards.

According to one embodiment of the invention, the analysis device comprises:
  a loading rotor disposed between the loading and unloading modules and of a substantially vertical axis of rotation, the loading rotor comprising a plurality of housings able to receive containers containing samples of biological liquid to be analyzed or reagent products, the sampling module being arranged to take samples or reagent products into the containers received in the loading rotor, and
  rotation driving means associated with the loading rotor and arranged to drive in rotation the loading rotor around its axis of rotation.

According to one embodiment of the invention, the loading rotor is removable.

According to one embodiment of the invention, each housing provided on the loading rotor opens into the upper face of the loading rotor.

According to one embodiment of the invention, at least two housings provided on the loading rotor have different dimensions. These dispositions enable the mounting of containers of different dimensions on the loading rotor.

According to one embodiment of the invention, the analysis device comprises a preparation and measuring module including:
  a preparation rotor of a substantially vertical axis of rotation, the preparation rotor comprising a plurality of preparation cuvettes, the sampling module being arranged to supply the preparation cuvettes with samples of biological liquid or reagent products previously taken, and
  rotation driving means associated with the preparation rotor and arranged to drive in rotation the preparation rotor around its axis of rotation.

Each preparation cuvette may for example extend in a plane substantially perpendicular to a diameter of the preparation rotor.

According to one embodiment of the invention, the middle of each preparation cuvette passes through a diameter of the preparation rotor.

According to one embodiment of the invention, the preparation cuvettes are distributed over the periphery of the preparation rotor, and preferably evenly distributed over the periphery of the preparation rotor.

Advantageously, at least one preparation cuvette has a rounded bottom, the concavity of which is turned upwards.

According to one embodiment of the invention, the preparation rotor is transparent. For example, the preparation rotor is made of transparent plastic material, such as the polymethyl methacrylate (PMMA).

The rotation driving means associated with the preparation rotor are advantageously arranged to drive in rotation the preparation rotor in a first direction and in a second direction opposite to the first direction. The rotation driving means associated with the preparation rotor are for example arranged to alternately drive in rotation the preparation rotor in the first and second directions, for example at an oscillation frequency corresponding to the natural oscillation frequency of the liquid contained in the preparation cuvette(s).

According to one embodiment of the invention, the rotation driving means associated with the preparation rotor include a stepper motor.

According to one embodiment of the invention, the preparation and measuring module comprises regulating means arranged to regulate the temperature of the preparation cuvettes at a determined level.

According to one embodiment of the invention, the preparation and measuring module includes at least one measuring and/or analysis station disposed around the preparation rotor. The at least one measuring and/or analysis station is for example a spectrophotometric reading module, a fluorescence reading module, a luminescence reading module, a coagulation measuring module.

According to one embodiment of the invention, the preparation rotor includes a rotary body on which the preparation cuvettes are removably mounted. According to one embodiment of the invention, the analysis device includes a supply station arranged to supply the rotary body with preparation cuvettes. These dispositions allow in particular to carry out whole-blood coagulation tests using the preparation rotor. Indeed, such tests involve the formation of a clot in the hardly washable preparation cuvette, and therefore are not feasible with a preparation rotor provided with irremovable preparation cuvettes.

According to one embodiment of the invention, the preparation rotor includes a rotary body on which the preparation cuvettes are arranged.

According to one embodiment of the invention, the at least one rack comprises windows enabling an optical reading of the identification codes carried by the containers received on said rack.

According to one embodiment of the invention, the sampling module includes a sampling head equipped with a sampling needle, first moving means arranged to move the sampling head in translation following a direction substantially horizontal and perpendicular to the guiding direction, and second moving means arranged to move the sampling head following a substantially vertical direction.

Advantageously, the sampling needle has a tip able to pierce the sealing elements of the containers received in the at least one rack.

According to one embodiment of the invention, the sampling module includes at least one rinsing well able to receive and rinse the sampling needle of the sampling head.

According to one embodiment of the invention, the loading and unloading modules include first and second guiding means arranged to cooperate with complementary guiding means provided on the at least one rack. The first and second guiding means include respectively for example a first and a second guiding rails able to cooperate with the complementary guiding means provided on the at least one container, and more particularly on the base of said rack.

According to one embodiment of the invention, the loading and unloading modules each have a storage capacity of at least fifteen racks.

According to one embodiment of the invention, each rack includes a plurality of housings substantially aligned in the plane of said rack and intended to receive one of the corresponding containers. In an advantageous manner, each housing comprises an introduction opening which opens outside of the rack and shaped to enable the introduction of the corresponding container in said housing. Each container is preferably removably mounted in the corresponding rack. According to one embodiment of the invention, each housing has a substantially circular section. In an advantageous manner, each container is mounted free in rotation in the corresponding housing.

BRIEF DESCRIPTION OF THE DRAWINGS

In any case the invention will be better understood using the description which follows with reference to the attached schematic drawing representing, as a non-limiting example, a form of execution of this analysis device.

DETAILED DESCRIPTION

The description below is given as an example of an embodiment of the invention and has no limitation.

Figure 1:
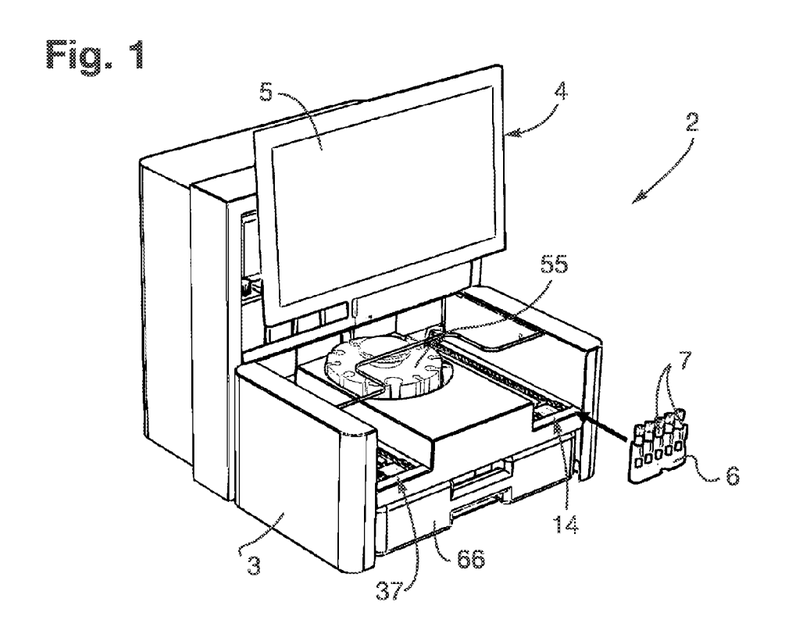
FIG. 1 is a frontal perspective view of an analysis device according to the invention.
Figure 2:
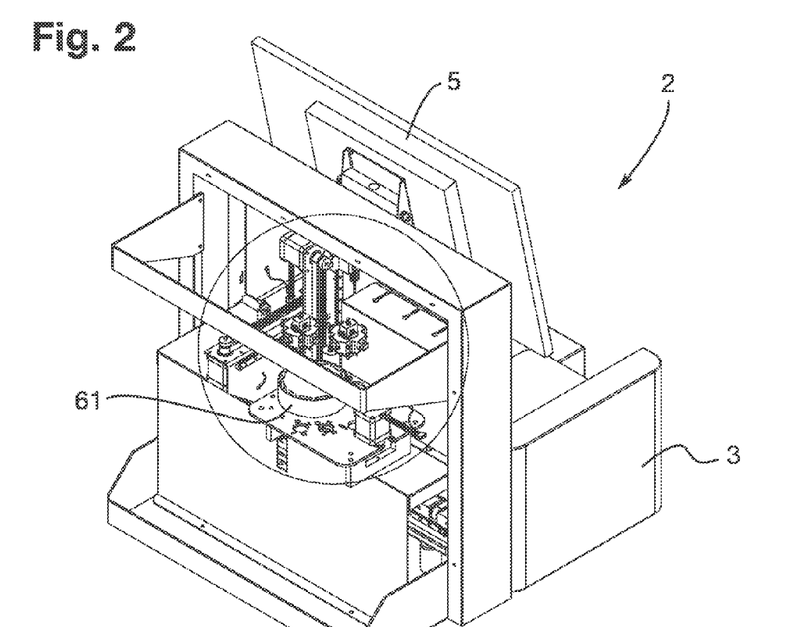
FIG. 2 is a partial rear perspective view of the analysis device of FIG. 1.

FIG. 1 represents an analysis device 2 for in vitro diagnosis, and more particularly to carry out blood tests, such as whole-blood tests.

The analysis device 2 comprises a frame 3, a communication and display interface 4 mounted on the frame 3, and an onboard electronics (not represented on the figures) housed in the frame 3.

The communication and display interface 4 includes for example a touch screen 5 connected to a PC computer. The PC computer is more particularly arranged to record analysis requests manually loaded by an operator using the touch screen 5 or from a central processing unit of an analysis laboratory, to send analysis queries to the onboard electronics, to recover measured data, process them using specific algorithms, and make the results available to the operator.

Figure 4:
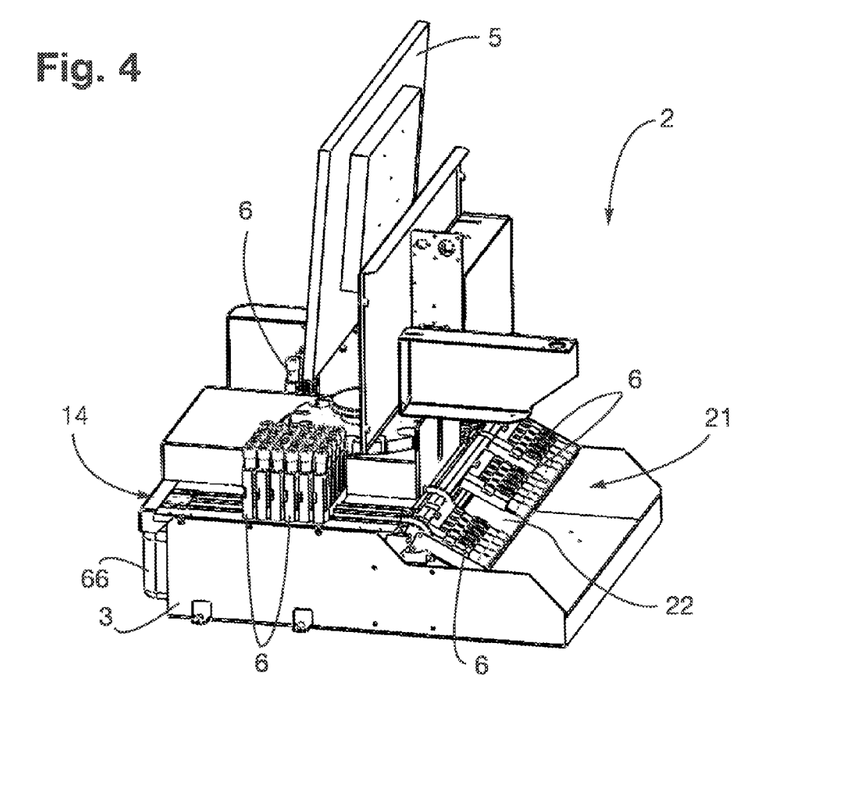
FIG. 4 is a partial side perspective view of the analysis device of FIG. 1.
Figure 8:
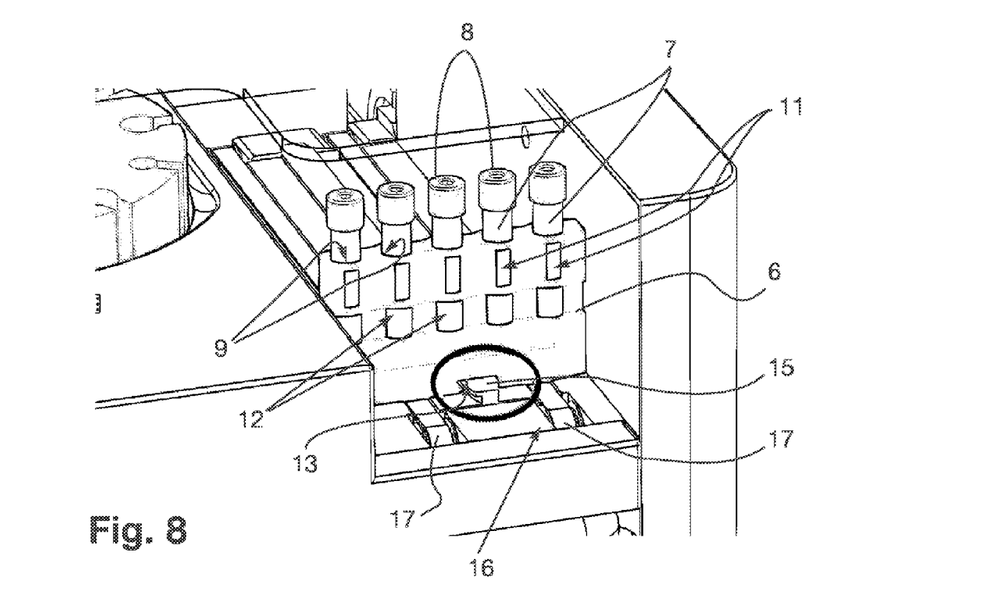
FIGS. 8 and 9 are partial perspective views of the analysis device of FIG. 1 showing more particularly the loading module belonging to said analysis device.

As shown more particularly on FIGS. 1, 4 and 8, the analysis device 2 comprises a plurality of racks 6, also called compartments or cassettes, intended to receive each a plurality of containers 7 equipped with sealing elements 8 and containing samples of biological liquid to be analyzed, such as blood samples. Advantageously, the containers 7 are sample tubes.

Each rack 6 has a generally parallelepiped shape and includes a plurality of housings 9, preferably cylindrical, aligned in the extension plane of said rack 6. The housings 9 are opened upwards in order to enable easy introduction and removal of the containers 7 into and out of the housings 9. Preferably, each housing 9 is shaped such that the corresponding container 7 is mounted free in rotation in said housing 9.

Each rack 6 also comprises a first series of windows 11 enabling an optical reading of identification codes carried by the containers 7, and a second series of windows 12 enabling a display of the content of said containers 7.

The base of each rack 6 further comprises a transverse notch 13 the function of which will be explained below.

As shown on FIG. 8, each rack 6 is provided to receive five containers 7. However, each rack 6 could be provided to receive less or more than five containers 7.

Figure 5:
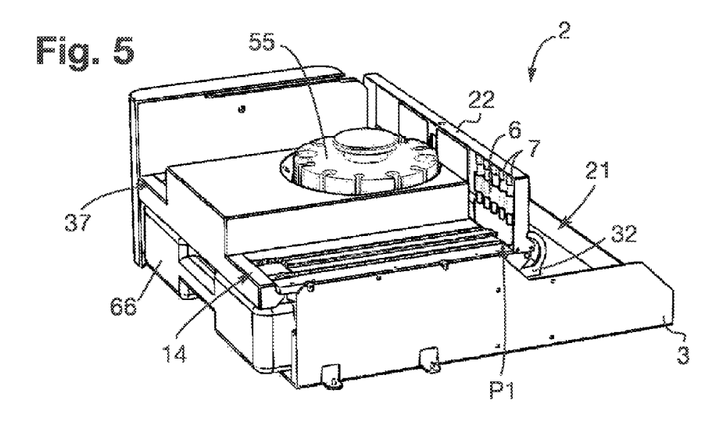
FIGS. 5 to 7 are partial side and perspective views of the analysis device of FIG. 1 showing more particularly a loading rotor and loading, unloading and shaking modules belonging to said analysis device.

The analysis device 2 further comprises a loading module 14 arranged to move each rack 6 loaded in the loading module 14 between a loading position P1 (see FIG. 5) and a first intermediate position P2 (see FIG. 10) along a first movement direction D1 horizontal and perpendicular to the extension plane of said rack 6.

The loading module 14 comprises a guiding rail 15 extending parallel to the first movement direction D1 and arranged to cooperate with the transverse notch 13 of each rack 6 loaded in the loading module 14 so as to guide in translation said rack during its movements between the loading position P1 and the first intermediate position P2. Advantageously, the guiding rail 15 has a dovetail section and the transverse notch 13 of each rack 6 has a complementary shape.

Figure 9:
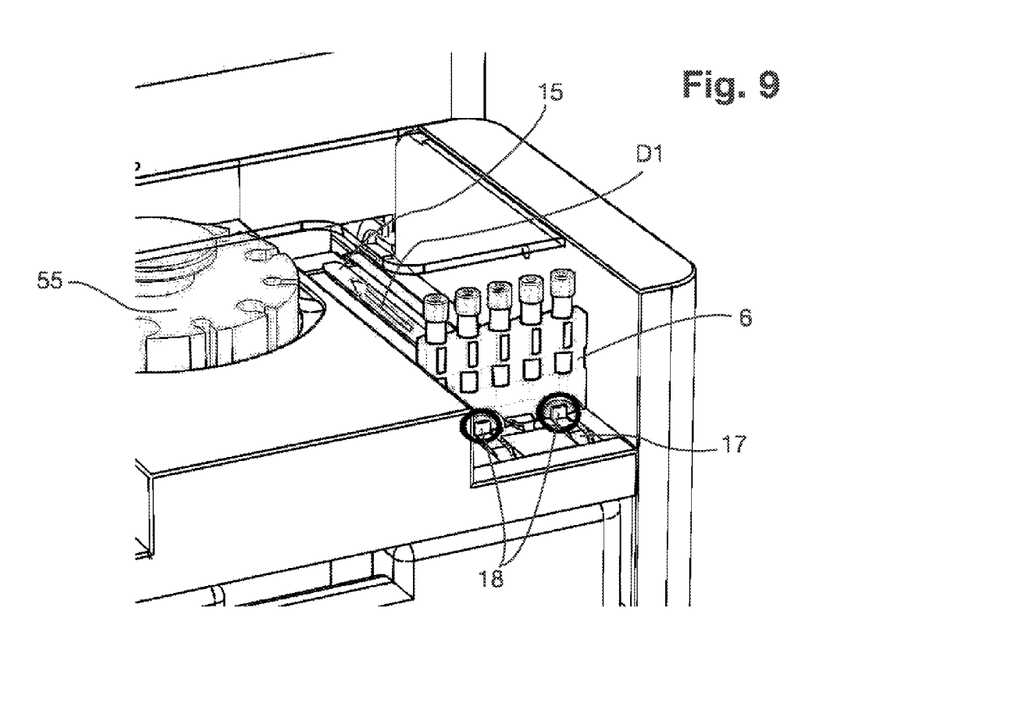

The loading module 14 comprises in addition a conveyor 16 comprising two conveyor belts 17 each equipped with a plurality of driving fingers 18 (shown on FIG. 9) arranged to cooperate with the base of each rack 6 loaded in the loading module 14 so as to drive in translation said rack between the loading position P1 and the first intermediate position P2.

Figure 11:
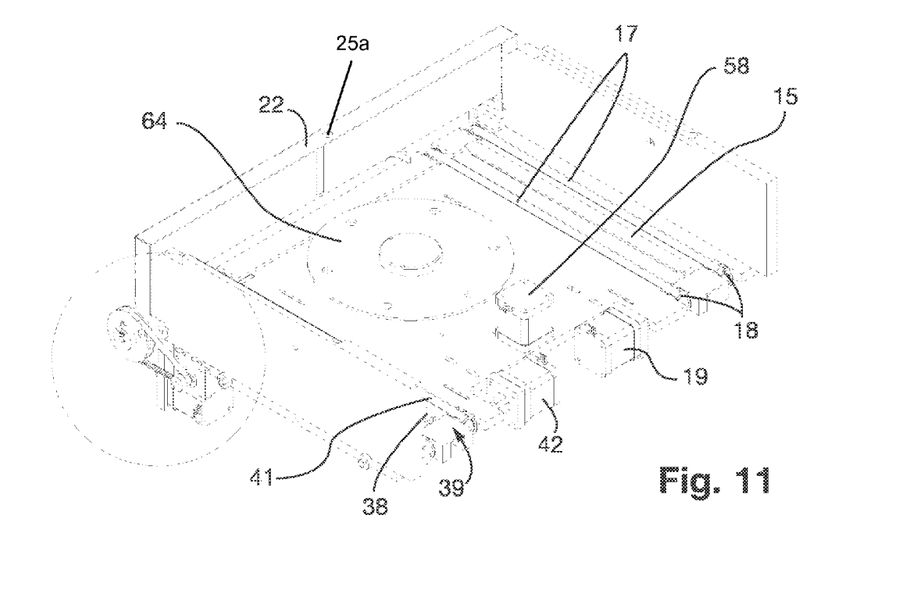
FIG. 11 is a partial perspective view of the analysis device of FIG. 1 showing more particularly the shaking module belonging to said analysis device.

The two conveyor belts 17 are driven by a motor 19 mounted on the frame 3 and more particularly represented on FIG. 11.

The analysis device 2 also comprises a shaking module 21 comprising a rack support 22 arranged to guide in translation at least one rack between the first intermediate position P2 and a second intermediate position P3 along a guiding direction D2 horizontal and perpendicular to the first movement direction D1.

The rack support 22 delimits a housing 23 in which at least one rack 6, and for example until three racks 6 simultaneously, is/are able to be introduced, preferably integrally.

The rack support 22 includes at least a first guiding wall 24 arranged to cooperate with a lateral wall of a rack 6 introduced into the housing 23, a second guiding wall 25 arranged to cooperate with the sealing elements 8 of the containers 7 received in the rack, and a third guiding wall 26 arranged to cooperate with a lower surface of the rack 6. The second guiding wall 25 is more particularly arranged to cooperate with the sealing elements 8 of the containers 7 received in the rack 6 so as to retain the containers 7 in the rack 6 during the pivoting of the rack support 22, and thus also forms a retaining wall. The second guiding wall 25 further includes a passage orifice 25a intended for the passage of a sampling needle.

The rack support 22 is pivotally mounted with respect to the frame 3 around a pivot axis A horizontal and parallel to the guiding direction D2.

Figure 6:
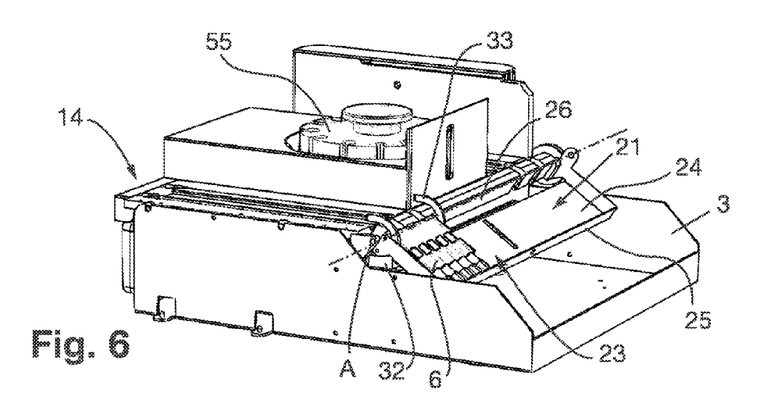
Figure 7:
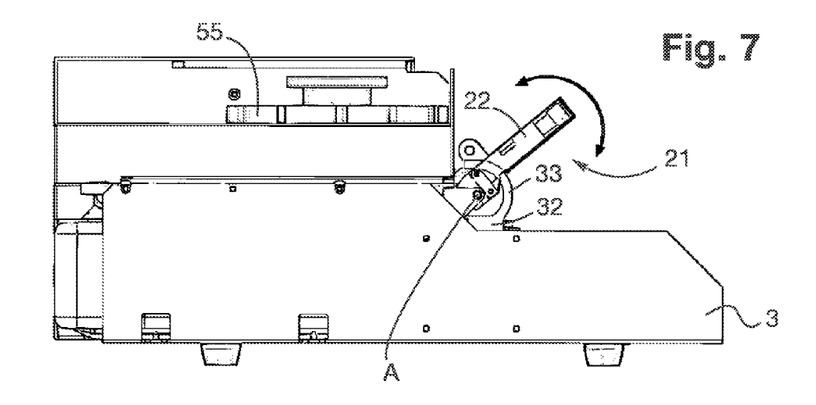

The shaking module 21 also comprises pivoting means arranged to pivotally drive the rack support 22 around the pivot axis A between a first angular position wherein the rack support 22 extends vertically (see FIG. 5) and a second angular position (see FIG. 6) wherein the rack support 22 is inclined relative to the vertical. The pivoting means are more particularly arranged to pivotally drive the rack support 22 around the pivot axis A along an angular displacement comprised between 0 and 160°, and for example between 0 and about 120°. As shown on FIGS. 5 and 6, the pivoting means are arranged to enable a tilting of a rack 6 loaded in the shaking module 21 between a position wherein the containers 7 received in the rack 6 are oriented upwards and a position wherein the containers 7 received in the rack 6 are oriented downwards.

Preferably the pivoting means are arranged to pivotally drive the support rack 22 along a swing movement around the pivot axis A. The pivoting means are for example arranged to generate at least twelve swings by minute of the rack support 22 around the pivot axis A, with preferably breaks between the swings so that the air bubble present in each container 7 received in a rack 6 loaded in the shaking module 21 can travel all the height of the container 7, and thus cause an optimal mixture of the sample contained in the container.

Figures 12, 13:
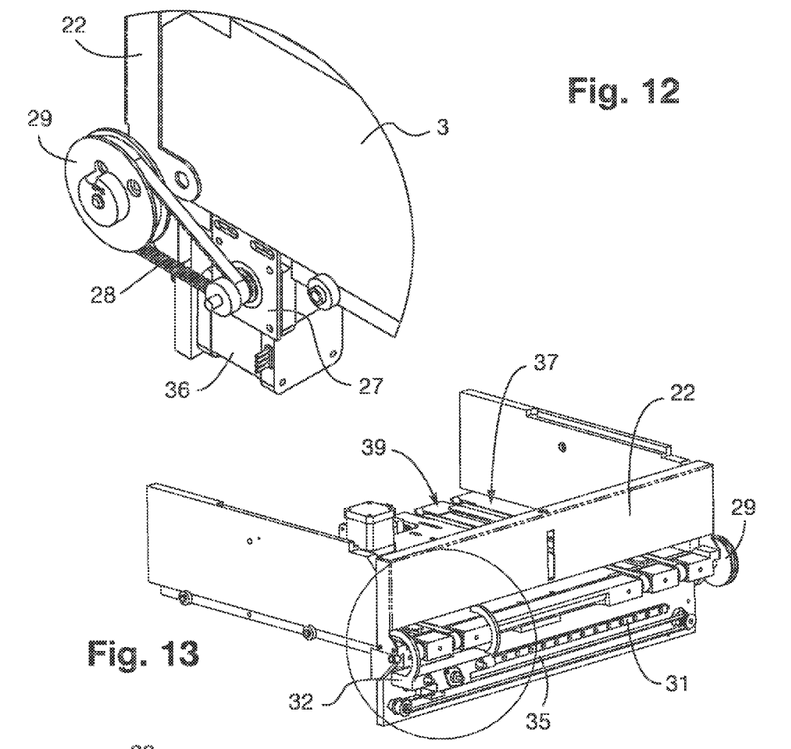
FIG. 12 is an enlarged scale view of a detail of FIG. 11.
FIG. 13 is a partial perspective view of the analysis device of FIG. 1 showing more particularly translational driving means belonging to said analysis device.

According to one embodiment represented in the figures, the pivoting means include a stepper motor 27 (see FIG. 12), the output shaft of which is coupled, for example by means of an endless belt 28, such as an endless toothed belt, to a pulley 29 secured in rotation to the rack support 22 and of axis coincident with the pivot axis A.

The shaking module 21 comprises in addition translational driving means arranged to drive in translation a rack 6 loaded in the shaking module 21 between the first and second intermediate positions P2, P3 along the guiding direction D2.

Figure 14:
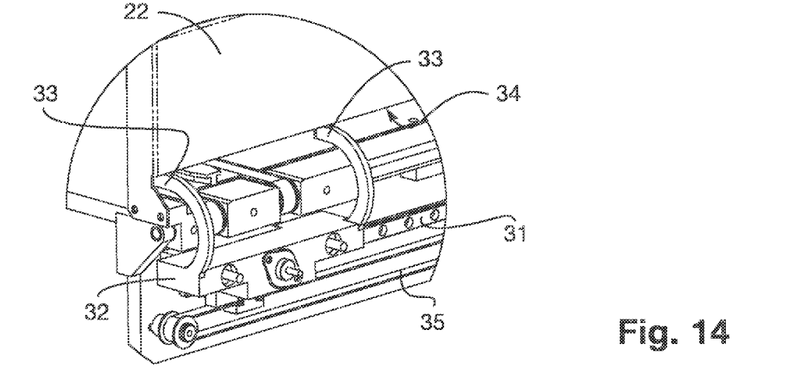
FIG. 14 is an enlarged scale view of a detail of FIG. 13.

According to the embodiment represented in the figures, the translational driving means include (see FIGS. 13 and 14) in particular a guiding rail 31 mounted on the frame 3 and extending parallel to the guiding direction D2, and a fork 32 slidably mounted on the guiding rail 31 and intended to cooperate with a rack 6 received in the housing 23 of the rack support 22. The fork 32 comprises in particular two parallel arms 33 spaced to one another by a distance substantially corresponding to the length of a rack 6, and intended to extend through a passage slot 34 arranged on the rack support 22.

The translational driving means also include an endless belt 35, such as an endless toothed belt, connected to the fork 32, and a driving motor 36 (see FIG. 12), the output shaft of which is provided with a pinion, preferably toothed, arranged to drive the endless belt 35.

According to one embodiment of the invention, the fork is provided with optical detecting means arranged to detect the insertion of a rack 6 in the housing 23 of the rack support 22, and the analysis device 2 is provided with control means connected to the detecting means and arranged to initiate the pivoting of the rack support 22 when the detecting means have detected the insertion of a rack 6 in the housing 23.

The rack support 22 and the translational driving means are preferably arranged to maintain each substantially vertical rack 6 during its movements along the guiding direction D2.

The analysis device 2 further comprises an unloading module 37 arranged to move a rack 6 between the second intermediate position P3 and an unloading position P4 along a second movement position D3 horizontal and perpendicular to the extension plane of said rack 6. The second movement direction D3 is advantageously parallel to the first movement direction D1 and perpendicular to the guiding direction D2.

The unloading module 37 is substantially identical to the loading module 14. Thus, the unloading module 37 also includes a guiding rail 38 extending parallel to the second movement direction D2 and arranged to cooperate with the transverse notch 13 of each rack 6 loaded in the unloading module 37 so as to guide in translation said rack during its movements between the second intermediate position P3 and the unloading position P4. The unloading module 37 further includes a conveyor 39 comprising two conveyor belts 41 each equipped with a plurality of driving fingers. The two conveyor belts 41 are driven by a motor 42 mounted on the frame 3 and more particularly represented on FIG. 11.

Figure 10:
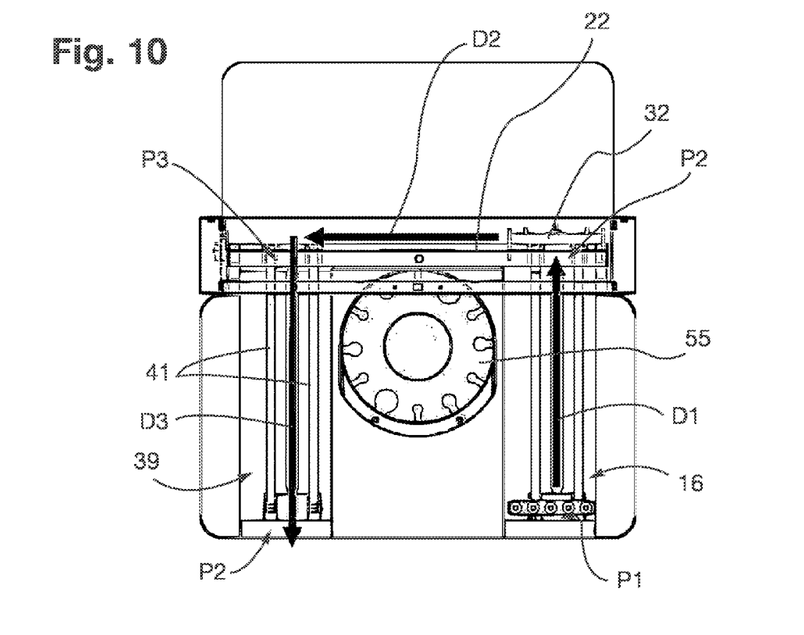
FIG. 10 is a partial top view of the analysis device of FIG. 1 showing more particularly the path of the racks between a loading position and an unloading position.

As shown on FIG. 10, the shaking 21, loading 14 and unloading 37 modules define a substantially horizontal generally U-shaped rack transport path. Such a configuration of the loading and unloading modules 14, 37 enables to ensure an automatic loading and unloading of the containers 6 into and out of the analysis device 2 for example by disposing the loading and unloading conveyors facing respectively the loading and unloading modules 14, 37.

The translational driving means are further arranged to vertically immobilize each rack received in the shaking module 21 in a plurality of sampling positions disposed between the first and second intermediate positions P2, P3, and more particularly in as much sampling positions as containers 7 received in said rack 6.

Figure 16:
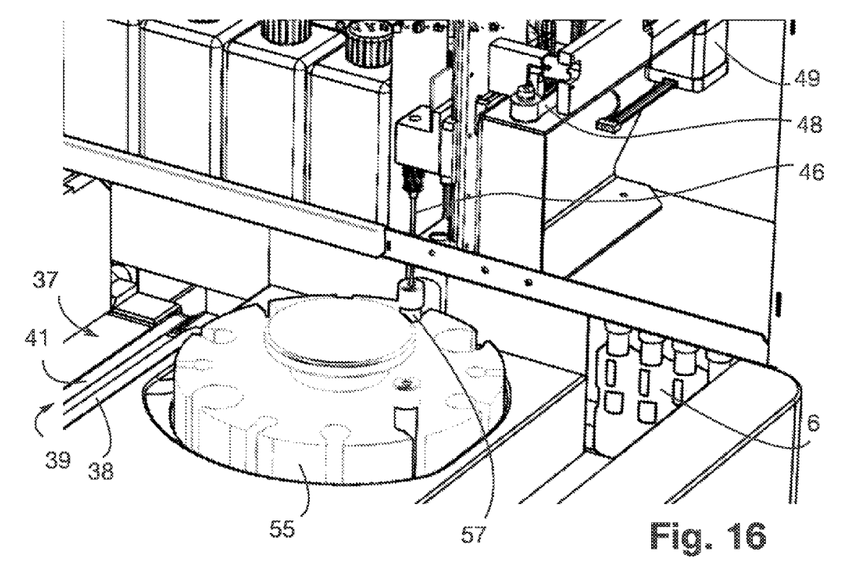
Figure 17:
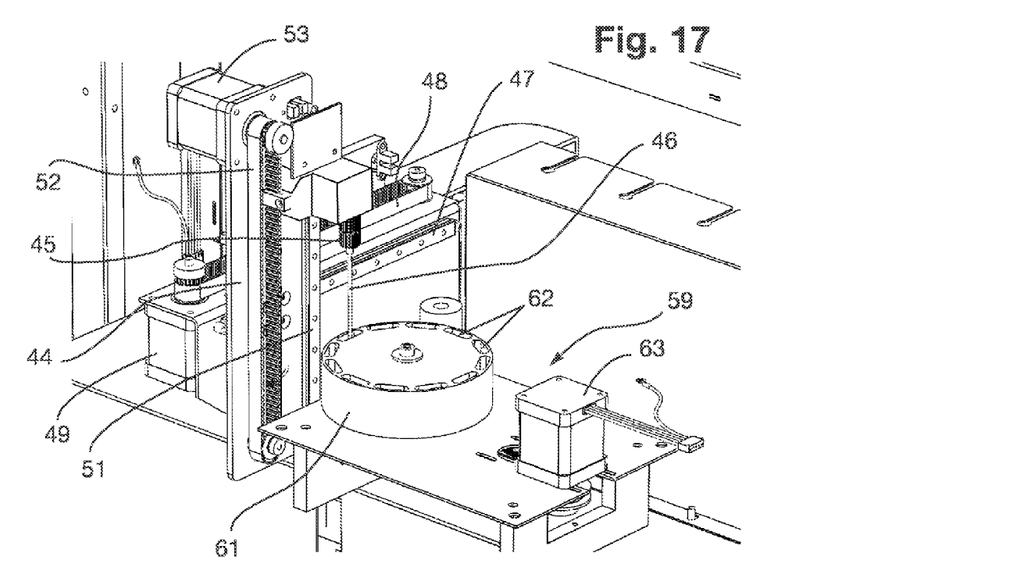
Figure 18:
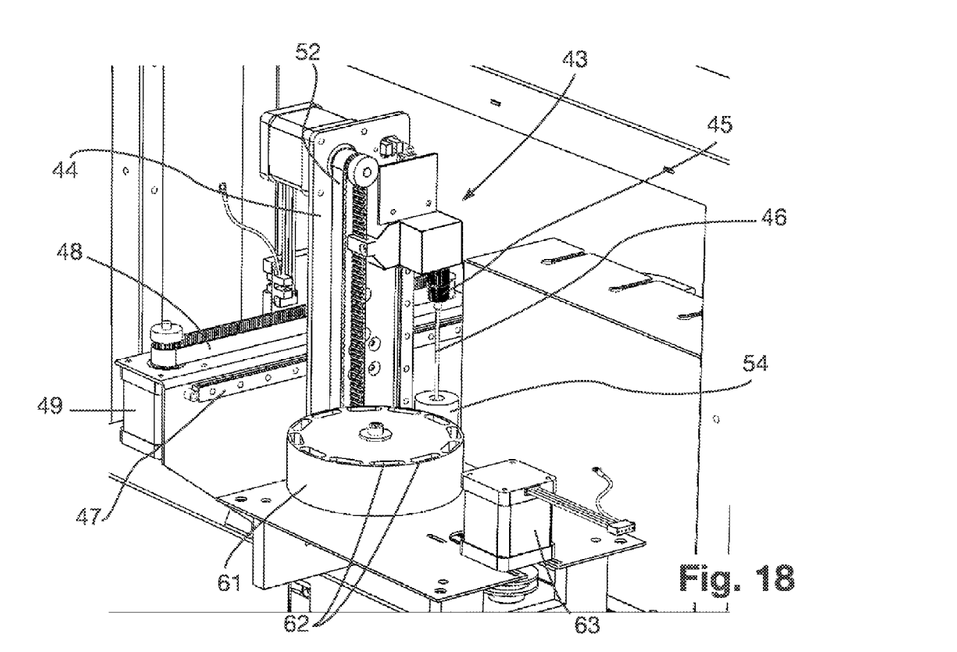
Figure 19:
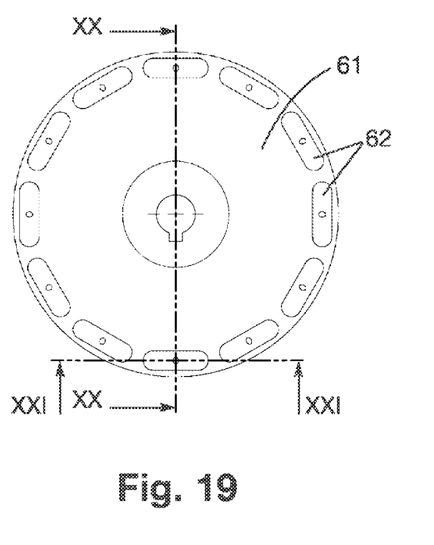
FIG. 19 is a top view of a preparation rotor belonging to the analysis device of FIG. 1.

The analysis device 2 comprises in addition a sampling module 43 disposed near the shaking module 21 (see FIGS. 16 to 18). The sampling module 43 is arranged to take samples of biological liquid in the containers 7 received in each rack 6 loaded in the shaking module 21. In particular, in each sampling position of a rack 6 loaded in the shaking module 21, the sampling module 43 is arranged to take a sample of biological liquid in one of the containers received in said rack 6.

The sampling module 43 includes in particular a sampling support 44, and a sampling head 45 mounted on the sampling support 44 and equipped with a sampling needle 46, the sampling needle 46 having a tip able to pierce the sealing elements 8 of the containers 7 received in each rack 6. The sampling module 43 further includes first moving means arranged to move the sampling head 44 in translation following a direction horizontal and perpendicular to the guiding direction D2, and second moving means arranged to move the sampling head 44 following a vertical direction.

Figure 15:
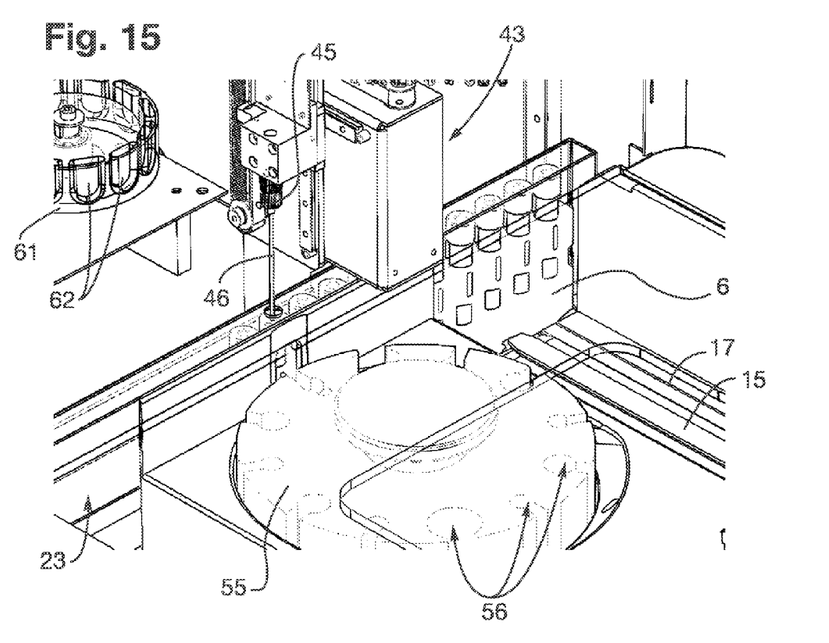
FIGS. 15 to 18 are partial perspective views of the analysis device of FIG. 1 showing different positions of the sampling head of a sampling module belonging to said analysis device.

As shown on FIG. 15, the first moving means comprise:
- a guiding rail 47 mounted on the frame and extending horizontally and perpendicular to the guiding direction D2, the sampling support 44 being slidably mounted on the guiding rail 47,
- an endless belt 48, preferably toothed, connected to the sampling support 44 and arranged to slidably drive the latter along the guiding rail 47, and
- a driving motor 49, the output shaft of which is provided with a pinion, preferably toothed, arranged to drive the endless belt 48.

As also shown on FIG. 15, the second moving means comprise:
- a guiding rail 51 mounted on the sampling support 44 and extending vertically, the sampling head 45 being slidably mounted on the guiding rail 51,
- an endless belt 52, preferably toothed, connected to the sampling head 45 and arranged to slidably drive the latter along the guiding rail 51, and
- a driving motor 53, the output shaft of which is provided with a pinion, preferably toothed, arranged to drive the endless belt 52.

The sampling module 43 includes in addition a rinsing well 54 able to receive and rinse the sampling needle 46 of the sampling head 45.

Advantageously, the sampling module 43 may further comprise level detecting means. Such detecting means enable on the one hand to avoid immersing systematically the sampling needle almost to the bottom of the containers as do most hematology analyzers, which contaminates nearly all of the length of the sampling needle, and on the other hand to be able to pipette with precision reagent products in vials. The level detecting means may for example include a capacitive detecting system.

As shown more particularly on FIGS. 15 and 16, the analysis device 2 comprises a loading rotor 55 disposed between the loading and unloading modules 14, 37 and of a substantially vertical axis of rotation. The loading rotor 55 comprises a plurality of housings 56 able to receive containers 57 containing samples of biological liquid to be analyzed or reagent products. Each housing 56 provided on the loading rotor 55 opens into the upper face of the loading rotor 55 in order to enable easy introduction and removal of the containers 57 into and out of the loading rotor 55. According to the embodiment represented on the figures, the loading rotor comprises housings 56 having different dimensions in order to enable the mounting of containers 57 of different dimensions on the loading rotor 55.

The analysis device 2 also comprises rotation driving means associated with the loading rotor 55 and arranged to drive in rotation the loading rotor 55 around its axis of rotation. The rotation driving means associated with the loading rotor 55 include for example a driving motor 58, such as a stepper motor, visible on FIG. 11.

As shown on FIG. 16, the sampling module 43 is arranged to take, using the sampling head 45, samples or reagent products in the containers 57 received in the loading rotor 55.

The loading rotor 55 enables to manually load and at any time in the analysis device, containers 57 containing samples to be analyzed and which should be manually shaken beforehand and/or vials of reagent products.

As shown more particularly on FIGS. 17 and 18, the analysis device 2 further comprises a preparation and measuring module 59 disposed inside the frame 3.

The preparation and measuring module 59 include in particular a preparation rotor 61 of a substantially vertical axis of rotation. As shown more particularly on FIGS. 19 to 22, the preparation rotor 61 comprises a plurality of preparation cuvettes 62 evenly distributed on the periphery of the preparation rotor 61.

As shown on FIG. 17, the sampling module 43 is arranged to supply the preparation cuvettes 62 with samples of biological liquid or with reagent products using the sampling head 45. Advantageously, the position of the sampling head 45 during the supply of the preparation cuvettes 62 is aligned with the positions of the sampling head 45 respectively during taking the liquid in a container 57 received in the loading rotor 55, during taking samples in a container 7 received in a rack 6, and during the rinsing of the sampling needle 46.

Each preparation cuvette 62 extends advantageously in a plane perpendicular to a diameter of the preparation rotor 61 and the middle of each preparation cuvette 62 passes through the corresponding diameter of the preparation rotor 61.

According to the embodiment represented in the figures, the preparation rotor 61 includes a rotary body on which the preparation cuvettes 62 are arranged. However, according to a variant not represented on the figures, the preparation rotor 61 can include a rotary body on which the preparation cuvettes are removably mounted. According to such a variant, the analysis device 2 would include a supply station arranged to supply the rotary body with preparation cuvettes.

Figure 20:
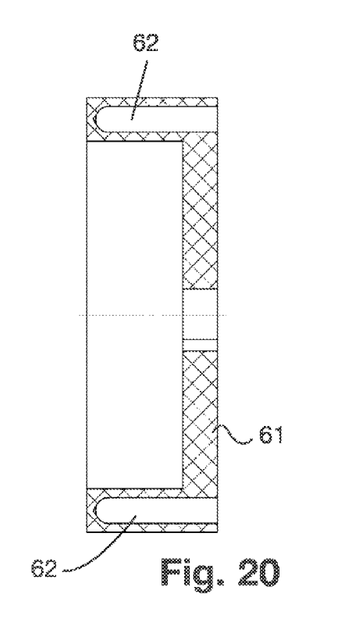
FIGS. 20 and 21 are sectional views respectively along the lines XX-XX and XXI-XXI of FIG. 19.
Figure 21:
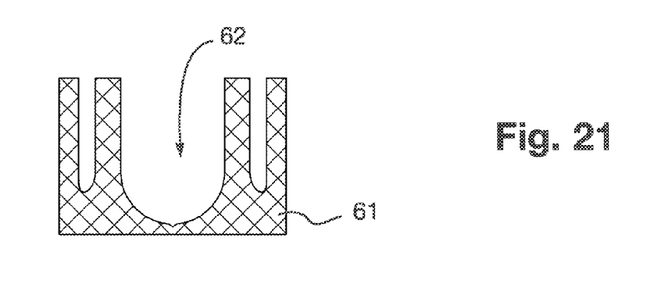

As shown on FIGS. 20 and 21, each preparation cuvette 62 has a rounded bottom, the concavity of which is turned upwards.

The preparation and measuring module 59 further includes rotation driving means associated with the preparation rotor 61. These rotation driving means are advantageously arranged to drive in rotation the preparation rotor 61 around its axis of rotation alternately in a first direction and in a second direction opposite to the first direction, for example at an oscillation frequency corresponding to the natural oscillation frequency of the liquid contained in the preparation cuvettes 62.

According to the embodiment represented in the figures, the rotation driving means associated with the preparation rotor 61 include a stepper motor 63 more particularly visible on FIG. 17.

The preparation and measuring module 59 may include advantageously regulating means arranged to regulate the temperature of the preparation cuvettes 62 at a determined level. As shown on FIG. 11, the regulating means may include in particular a thermally conductive metal plate 64 disposed under the preparation rotor 61 and heating means arranged to heat the thermally conductive metal plate 64.

The preparation rotor 61 is made for example of transparent plastic material, such as polymethyl methacrylate (PMMA). These dispositions enable to perform different measurements through the material of the preparation rotor 61, such as photometry measurements.

Thus, the analysis device comprises advantageously at least one measuring station disposed around the preparation rotor 61, such as a photometric measuring station adapted to measure in particular the level of hemoglobin in the sample to be analyzed, or even the level of D-dimers or of CRP in the sample to be analyzed.

The analysis device 2 may further comprise also a spectrophotometric reading module, a fluorescence reading module, a luminescence reading module or even a coagulation measuring module disposed around the preparation rotor 61.

Figure 3:
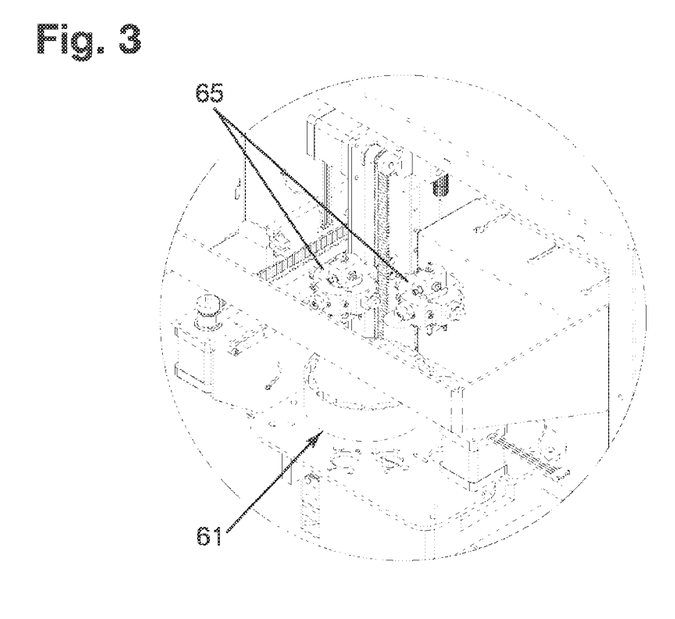
FIG. 3 is an enlarged scale view of a detail of FIG. 2.

As shown on FIG. 3, the analysis device 2 may further include one or more cytometric measuring head(s) 65 which enable to carry out with precision all the hematology measurements relative to the complete blood count. The analysis device 2 can for example include a first cytometric measuring head 65 to carry out measurements of red blood cells or platelets, and a second cytometric measuring head 65 to carry out measurements of white blood cells. These dispositions enable to carry out measurements in parallel, and therefore to increase the analysis rate of the analysis device 2 according to the invention.

It must be noted that the analysis device 2 also includes a flat canister 66 disposed under the loading and unloading modules 14, 37, and intended to contain isotonic dilution liquid acting as liquid system. The flat canister 66 is advantageously provided with a rubber plug pierced automatically at the end of travel by an appropriate piercing member, which makes both the liquid system available to the analysis device 2, but also enables air venting. Advantageously, the liquid system will be heated by known devices. The canister intended to accommodate used liquid is not represented on the figures.

The operation of the analysis device 2 is as follows.

Racks 6 provided with containers 7 containing samples of biological liquid to be analyzed are manually or automatically loaded in the loading module 14. These racks 6 are successively brought till the rack support 22 for their shaking using the shaking module 21.

After shaking, each rack 6 is then moved in a first sampling position. The sampling head 45 of the sampling module 43 is then moved so that the sampling needle 46 passes through the passage orifice 25a provided on the second guiding wall 25 and takes a predetermined sample volume of biological liquid to be analyzed in a first container 7 received in the rack 6 immobilized in the first sampling position. When removing the sampling needle 46 out of the first container 7, the second guiding wall 25, which cooperates with the sealing element 8 of the first container 7, maintains the first container 7 in the housing 23 of the rack support 22.

The sampling head 45 of the sampling module 43 is then moved so that the sampling needle 46 introduces the predetermined sample volume in a preparation cuvette 62 of the preparation rotor 61. Then, the liquid system taken from the flat canister 66 is introduced, using an appropriate supply station, in said preparation cuvette 62 in order to make a first dilution of the biological liquid to be analyzed.

In order to ensure a homogeneous mixture of the liquid system and of the biological liquid to be analyzed, the preparation rotor is put in rotation around its axis of rotation alternately in a first direction S1 and in a second direction S2 opposite to the first direction S1, according to an oscillation frequency corresponding substantially to the natural oscillation frequency of the contained mixture in the preparation cuvette 62.

Figure 22:
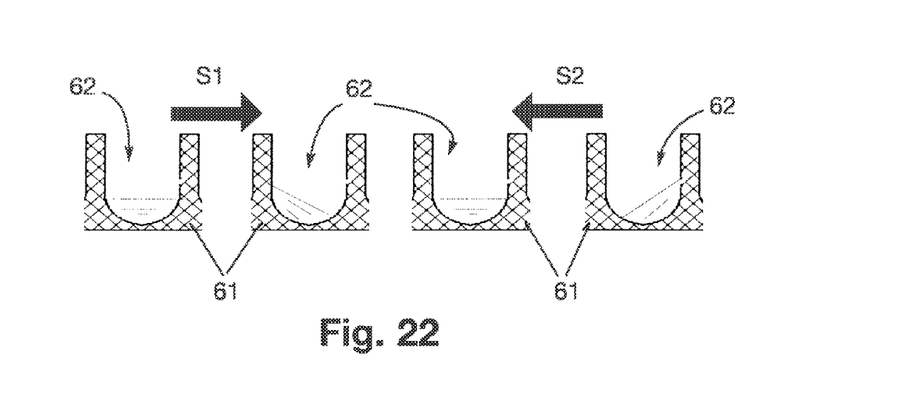
FIG. 22 is a schematic view showing the movement of the liquid in a preparation cuvette of the preparation rotor when the preparation rotor is driven with reciprocating movements of low amplitude.

Such reciprocating movements of rotation of the preparation rotor 61 generate movements of the liquids contained in the preparation cuvette 62 such as shown on FIG. 22 and ensure an optimal mixture of these liquids, and this due to the disposition of the preparation cuvettes 62 relative to the axis of rotation of the preparation rotor and of the shape of the preparation cuvettes 62. It should be noted that the lateral walls of the preparation cuvettes are high enough to avoid liquid overflows during these oscillations.

If necessary, the obtained mixture is sucked by the sampling needle 46 and distributed in an empty preparation cuvette 62, for example to carry out a second dilution. When the dilution step is completed, the preparation rotor is driven in rotation in order to position the preparation cuvette 62 containing the mixture to be analyzed facing a distribution station of Lysis reagents to obtain solutions ready for carrying out hematological measurements.

When the different actions to be carried out on the relevant sample are carried out, the different preparation cuvettes 62 are rinsed using an appropriate rinsing station if they are irremovable, or they are replaced by other preparation cuvettes if they are disposable, for the analysis of another container 7 received in the rack 6 in sampling position.

When the sample contained in the aforementioned first container 7 has been analyzed, the translational driving means move the corresponding rack 6 in a second sampling position, so as to enable making a sample in a second container 7 housed in said rack 6 and to carry out, using the sampling module 43, the analysis of this sample. These steps are repeated so as to enable the analysis of samples contained in the different containers 7 received in the rack 6.

When the samples contained in the different containers 7 housed in the disposed rack 6 have been analyzed, the rack 6 is moved in the second intermediate position P3 for its unloading using the unloading module 37. However, if necessary, the rack 6 may be brought into a sampling position by reversing the direction of operation of the driving motors 36, 42 in order to carry out a new analysis of a sample contained in one of the containers housed in said rack 6.

Furthermore, the analysis device 2 enables to carry out specific or urgent analyses using the loading rotor 55 by placing containers 57 therein containing samples of biological liquid to be analyzed or specific reagent products. In such a case, the loading rotor 55 is driven in rotation to dispose the desired container 57 in a predetermined position (see FIG. 16) enabling to take the liquid contained in the latter using the sampling needle 46, this liquid being then introduced into a preparation cuvette 62 of the preparation rotor 61.

As it goes without saying that the invention is not limited to the sole form of execution of this analysis device, described above by way of example, on the contrary, it encompasses all the variants.

The invention claimed is:
1. An analysis device for in vitro diagnosis, comprising:
at least one rack intended to receive a plurality of containers equipped with sealing elements and containing samples of biological liquid to be analyzed,
a loading module configured to move the at least one rack between a loading position and a first intermediate position along a first movement direction transverse to the plane of the at least one rack,
a shaking module configured to move the at least one rack between the first intermediate position and a second intermediate position and to shake the at least one rack, the shaking module being arranged such that the at least one rack extends substantially along a same orientation in the first and second intermediate positions,
an unloading module configured to move the at least one rack between the second intermediate position and an unloading position along a second movement direction transverse to the plane of the at least one rack, and a sampling module configured to take samples of biological liquid in the containers received in the at least one rack, a loading rotor disposed between the loading and unloading modules, the loading rotor having a substantially vertical axis of rotation and comprising a plurality of housings able to receive containers containing samples of biological liquid to be analyzed or reagent products, the sampling module being arranged to take samples or reagent products in the containers received in the loading rotor, a preparation and measuring module including a preparation rotor having a substantially vertical axis of rotation, the preparation rotor comprising a plurality of preparation cuvettes, the sampling module being arranged to supply the preparation cuvettes with samples of biological liquid or reagent products previously taken, the measuring module including at least one measurement device disposed around the preparation rotor, the shaking module including:

a rack support configured to guide in translation the at least one rack from the first intermediate position to the second intermediate position along a guiding direction, the rack support being pivotally mounted around a pivot axis, the rack support delimiting a housing wherein the at least one rack is able to slide along the guiding direction, the rack support including a first guiding wall cooperating with a lateral wall of the at least one rack during the sliding of said at least one rack in the housing of the rack support, and a retaining wall cooperating with sealing elements of containers received in said at least one rack so as to retain the containers in said at least one rack during the pivoting of the rack support, the retaining wall including a passage orifice for the passage of a sampling needle of the sampling module, translational driving means configured to drive in translation the at least one rack between the first and second intermediate positions along said guiding direction, and pivoting means configured to pivotally drive the rack support around the pivot axis.

2. The analysis device according to claim 1, wherein the loading and unloading modules maintain the at least one rack substantially vertical during its movements along the first and second movement directions.

3. The analysis device according to claim 1, wherein the shaking module maintains the at least one rack substantially vertical during its movements between the first and second intermediate positions.

4. The analysis device according to claim 1, wherein the shaking module and the loading and unloading modules define a generally U-shaped rack transport path.

5. The analysis device according to claim 1, wherein each preparation cuvette extends in a plane substantially perpendicular to a diameter of the preparation rotor.

6. The analysis device according to claim 1, wherein each preparation cuvette has a rounded bottom, the concavity of which is turned upwards.

7. The analysis device according to claim 1, wherein the preparation rotor is transparent.

8. The analysis device according to claim 1, wherein at least two housings provided on the loading rotor have different dimensions.

9. The analysis device according to claim 1, wherein the preparation rotor is alternatively rotatable in a first direction and in a second direction opposite to the first direction.

10. The analysis device according to claim 1, wherein the housing delimited by the rack support is arranged to simultaneously house a plurality of racks.

11. The analysis device according to claim 1, wherein the housing delimited by the rack support includes a rack introduction portion and a rack removal portion, the first and second intermediate positions corresponding respectively to an insertion position of a rack into the rack introduction portion and to a removal position of a rack out of the rack removal portion.

12. The analysis device according to claim 1, wherein the housing of the rack support is partially defined by the first guiding wall and the retaining wall of the rack support.

13. The analysis device according to claim 1, wherein the housing delimited by the rack support is configured to entirely receive the at least on rack.

14. The analysis device according to claim 1, wherein the retaining wall extends substantially perpendicularly from the first guiding wall.

15. The analysis device according to claim 1, further including detecting means arranged to detect the insertion of the at least one rack in the housing of the rack support.

* * * * *